United States Patent
Li et al.

(10) Patent No.: US 12,387,296 B2
(45) Date of Patent: Aug. 12, 2025

(54) SYSTEMS AND METHODS FOR ARTIFACT REDUCTION IN TOMOSYNTHESIS WITH MULTI-SCALE DEEP LEARNING IMAGE PROCESSING

(71) Applicant: The General Hospital Corporation, Boston, MA (US)

(72) Inventors: Quanzheng Li, Boston, MA (US); Kyungsang Kim, Boston, MA (US); Dufan Wu, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 358 days.

(21) Appl. No.: 17/759,801

(22) PCT Filed: Feb. 1, 2021

(86) PCT No.: PCT/US2021/015999
§ 371 (c)(1),
(2) Date: Jul. 29, 2022

(87) PCT Pub. No.: WO2021/155340
PCT Pub. Date: Aug. 5, 2021

(65) Prior Publication Data
US 2023/0061863 A1    Mar. 2, 2023

Related U.S. Application Data

(60) Provisional application No. 62/968,457, filed on Jan. 31, 2020.

(51) Int. Cl.
*G06T 5/70*    (2024.01)

(52) U.S. Cl.
CPC ...... *G06T 5/70* (2024.01); *G06T 2207/10112* (2013.01); *G06T 2207/20081* (2013.01);
(Continued)

(58) Field of Classification Search
CPC ............ G06T 5/70; G06T 2207/10112; G06T 2207/20081; G06T 2207/20084;
(Continued)

(56) References Cited

U.S. PATENT DOCUMENTS 10,817,990 B1 *  10/2020  Yang ............... H04N 19/154
10,949,951 B2 *  3/2021  Tang ............... G16H 30/20
(Continued)

OTHER PUBLICATIONS

Y. Choi, H. Shim and J.Baek, "Image Quality Enhancement of Digital Breast Tomosynthesis Images by Deblurring with Deep Residual Convolutional Neural Network," 2018 IEEE Nuclear Science Symposium and Medical Imaging Conference Proceedings (NSS/MIC), Sydney, NSW, Australia, 2018, pp. 1-3, doi: 10.1109/N (Year: 2018).*

(Continued)

*Primary Examiner* — Santiago Garcia
(74) *Attorney, Agent, or Firm* — QUARLES & BRADY LLP (57) ABSTRACT

Systems and methods are provided for a multi-scale deep learning-based digital breast tomosynthesis (DBT) image reconstruction that mitigates the superposition of breast tissue along with the limited angular artifacts, and improves in-depth resolution of the resulting images. A multi-scale deep neural network may be used where a first network may focus on a first parameter, such as limited angular artifacts reduction, and a second network may focus on a second parameter, such as image detail refinement. The output from the first neural network may be used as the input for the second neural network. The systems and methods may reduce the sparse-view artifacts in DBT via deep learning without losing image sharpness and contrast. A deep neural network may be trained in a way to reduce training-time computational cost. An ROI loss method may be used for
(Continued)

further improvement on the resolution and contrast of the images.

27 Claims, 5 Drawing Sheets

(52) U.S. Cl.
CPC ............... *G06T 2207/20084* (2013.01); *G06T 2207/30068* (2013.01)

(58) Field of Classification Search
CPC .......... G06T 2207/30068; A61B 6/025; A61B 6/5258; A61B 6/502
See application file for complete search history.

(56) References Cited

U.S. PATENT DOCUMENTS

| | | | |
|---|---|---|---|
| 2006/0241423 A1 | 10/2006 | Anderson | |
| 2007/0014480 A1 | 1/2007 | Sirohey | |
| 2009/0175562 A1* | 7/2009 | Pan | A61B 6/5288 382/312 |
| 2009/0196493 A1* | 8/2009 | Widrow | G06N 3/02 707/999.005 |
| 2014/0037044 A1 | 2/2014 | Ning | |
| 2014/0294138 A1 | 10/2014 | Jerebko | |
| 2016/0146910 A1* | 5/2016 | Kaneko | A61B 5/055 324/309 |
| 2017/0200067 A1 | 7/2017 | Zhou et al. | |
| 2019/0108634 A1* | 4/2019 | Zaharchuk | G06N 3/08 |
| 2019/0139216 A1* | 5/2019 | Georgescu | G06N 3/048 |
| 2019/0325621 A1 | 10/2019 | Wang et al. | |
| 2020/0020097 A1 | 1/2020 | Do et al. | |
| 2020/0065940 A1* | 2/2020 | Tang | G06T 3/40 |
| 2020/0242744 A1* | 7/2020 | Schafer | G06T 5/60 |
| 2020/0294287 A1* | 9/2020 | Schlemper | G06V 10/431 |
| 2020/0397334 A1* | 12/2020 | Fang | G06N 3/08 |
| 2021/0082184 A1* | 3/2021 | Claessen | G06T 17/20 |
| 2021/0097297 A1* | 4/2021 | Ren | G06N 3/047 |
| 2021/0118199 A1* | 4/2021 | Chui | G16H 50/20 |
| 2022/0180518 A1* | 6/2022 | Agus | G16H 50/70 |
| 2022/0245792 A1* | 8/2022 | Gao | G06T 7/0008 |
| 2022/0287687 A1* | 9/2022 | Liao | A61B 6/4417 |
| 2024/0127437 A1* | 4/2024 | Anand | G06V 10/25 |

OTHER PUBLICATIONS

Y. Choi, H. Shim and J. Baek, Image Quality Enhancement of Digital Breast Tomosynthesis Images by Deblurring with Deep Residual Convolutional (Year: 2018).*

Adler, J., et al., "Learned Primal-Dual Re-construction," IEEE Transactions on Medical Imaging (2018) pp. 1322-1332, vol. 37, No. 6.

Bakic, P.R., et al., "Development and characterization of an anthropomorphic breast software phantom based upon region-growing algorithm," Medical Physics (2011) pp. 3165-3176, vol. 38, No. 6.

Desantis, C.E., et al., "Breast cancer statistics, 2017, racial disparity in mortality by state," CA: A Cancer Journal for Clinicians (2017) pp. 439-448, vol. 67, No. 6.

Elbakri, I. A., et al., "Statistical image reconstruction for polyenergetic X-ray computed tomography." IEEE transactions on medical imaging (2002) pp. 89-99, vol. 21, No. 2.

Erickson, D.W., et al., "Population of 224 realistic human subject-based computational breast phantoms," Medical Physics (2016) pp. 23-32, vol. 43, No. 1.

Gur, D., et al., "Digital breast tomosynthesis: Observer performance study," American Journal of Roentgenology (2009) pp. 586-591, vol. 193, No. 2.

Kim, K., et al., "Fully iterative scatter connected digital breast tomosynthesis using GPU-based fast Monte Carlo simulation and composition ratio update," Medical Physics (2015) pp. 5342-5355, vol. 42, No. 9.

Moriakov, N., et al., "Deep learning frame-work for digital breast tomosynthesis reconstruction," Medical Imaging 2019: Physics of Medical Imaging, H. Bosmans, G.-H. Chen, and T. Gilat Schmidt, Eds., SPIE (2018) p. 220, vol. 10948.

Parikh, N., "Proximal Algorithms," Foundations and Trends® in Optimization (2013) pp. 127-239, vol. 1, No. 3.

Su, et al., "DIR-DBTnet: Deep iterative reconstruction network for 3D digital breast tomosynthesis imaging" arXiv:2008.08322, Aug. 20, 2020. Retrieved on Apr. 5, 2021. Retrieved from <URL: https://arxiv.org/pdf/2008.08322.pdf> entire document.

Wu, D., et al., "Computationally Efficient Deep Neural Network for Computed Tomography Image Reconstruction," Medical Physics (2019) p. mp. 13627.

Wu, D., et al., "Digital Breast Tomosynthesis Reconstruction with Deep Neural Network for Improved Contrast and In-Depth Resolution," IEEE 17th International Symposium on Biomedical Imaging (ISBI), (2020) pp. 656-659, Iowa City, IA, USA, 2020, doi: 10.1109/ISBI45749.2020.9098661.

International Search Report of the International Searching Authority pertaining to International Application No. PCT/US2021/015999; Date of Mailing: Apr. 22, 2021.

Written Opinion of the International Searching Authority pertaining to International Application No. PCT/US2021/015999; Date of Mailing: Apr. 22, 2021.

\* cited by examiner

SYSTEMS AND METHODS FOR ARTIFACT REDUCTION IN TOMOSYNTHESIS WITH MULTI-SCALE DEEP LEARNING IMAGE PROCESSING

CROSS-REFERENCE TO RELATED APPLICATIONS

This application represents the U.S. national stage entry of PCT International Application No. PCT/US2021/015999 filed Feb. 1, 2021, which claims the benefit of U.S. Provisional Patent Application Ser. No. 62/968,457 filed on Jan. 31, 2020 and entitled "System and Method of Superposition Artifacts Reduction in and Image Contrast Improvement of Digital Breast Tomosynthesis with Deep-Learning-Based Image Processing/Reconstruction," the contents of each of which are incorporated herein by reference as if set forth in its entirety for all purposes.

STATEMENT REGARDING FEDERALLY SPONSORED RESEARCH

N/A

BACKGROUND

Breast cancer is the second most common cancer in women. It is also the second leading cause of cancer death among American women. Evidence has shown that screening and early detection is the key to prevent breast cancer death. Screening is conventionally performed using mammography, which provides for 2D imaging, but the breast tissue depicted may be overlapping due to a single view angle. Digital breast tomosynthesis (DBT) is an emerging, promising new technology for breast cancer screening imaging that takes several images from different angles, which may be from different depths that may be stacked to form a 3D image. Compared to the conventional X-ray mammography, DBT has significantly improved sensitivity and specificity. Meanwhile, DBT has very similar hardware setup with mammography, which lowers the cost for both manufacturers and users to upgrade from mammography to DBT.

Digital breast tomosynthesis (DBT) provides 3D reconstruction that reduces the superposition and overlapping of breast tissues compared to mammography, leading to increased sensitivity and specificity. However, to save dose and scanning time, most DBT system has large sampling interval (≥3°) and a very limited angular sampling range of ≤50°. The resulting superposition of breast tissues may still be severe. The large angular interval also leads to sparse-view artifacts, where streaks due to high-contrast objects are visible in the DBT images. The artifacts cause ambiguity in some cases when they are overlapping with local structures. The obvious artifacts also lowered physician's confidence when making decision with the DBT images. DBT images also may suffer from limited in-depth resolution.

3D DBT also has very high resolution, which leads to huge training computational cost. Thus, there remains a need for a DBT reconstruction method to mitigate the limited angular artifacts and superposition of breast tissue, while improving in-depth resolution and avoiding computational cost burdens.

SUMMARY OF THE DISCLOSURE

The present disclosure addresses the aforementioned drawbacks by providing systems and methods for a multi-scale deep learning-based tomosynthesis reconstruction that mitigates limited angular artifacts and superposition of tissue, and improves in-depth resolution. A multi-scale deep neural network may be used where a first, or low-resolution, network may focus on a first parameter, such as limited angular artifacts reduction, and a second, or high-resolution, network may focus on a second parameter, such as image detail refinement. The output from the first neural network may be used as the input for the second neural network. The systems and methods can reduce the sparse-view artifacts in DBT via deep learning without clinically damaging image sharpness and contrast. A deep neural network may be trained, such as an unroll-type neural network, and may be used with a decoupled training for each unroll to reduce training-time computational cost.

In one configuration, a digital breast tomosynthesis system is provided for controlling artifacts in imaging of a subject. The system includes a base plate, and a compression plate configured to provide compression of an organ disposed between the base plate and the compression plate. The system also includes a rotation support coupled to the base plate and the compression plate to rotate the base plate and the compression plate about the organ to acquire digital breast tomosynthesis image data with a plurality of resolutions. The system also includes a computer system configured to: access a trained multi-scale neural network including a first resolution network and a second resolution network. The first resolution network or the second resolution network may be trained to suppress artifacts using image training data that include at least one artifact. A first resolution of the first resolution network is lower than a second resolution of the second resolution network. The computer system is also configured to: access the acquired digital breast tomosynthesis image data of the subject that includes a region of interest of the organ; subject the acquired digital breast tomosynthesis image data to the trained multi-scale neural network to reconstruct an image of the subject with suppressed artifacts in the region of interest; and display the image of the subject with the suppressed artifacts.

In one configuration, a method is provided for artifact reduction in digital breast tomosynthesis imaging of a subject. The method includes accessing a trained multi-scale neural network including a first resolution network and a second resolution network. The first resolution network or the second resolution network may be trained to suppress artifacts using image training data that include at least one artifact. A first resolution of the first resolution network is lower than a second resolution of the second resolution network. The method also includes accessing digital breast tomosynthesis image data of the subject that includes a region of interest and subjecting the digital breast tomosynthesis image data to the multi-scale neural network to reconstruct an image of the subject with suppressed artifacts in the region of interest. The method also includes displaying the image of the subject with the suppressed artifacts.

In one configuration, a system is provided for artifact reduction in digital breast tomosynthesis imaging of a subject. The system includes a computer system configured to access a trained multi-scale neural network including a first resolution network and a second resolution network. The first resolution network or the second resolution network may be trained to suppress artifacts using image training data that include at least one artifact. A first resolution of the first resolution network is lower than a second resolution of the second resolution network. The computer system is also configured to access digital breast tomosynthesis image data of the subject that includes a region of interest and subject the digital breast tomosynthesis image data to the multi-scale neural network to reconstruct an image of the subject with suppressed artifacts in the region of interest. The computer system is also configured to display the image of the subject with the suppressed artifacts.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention. Like reference numerals will be used to refer to like parts from Figure to Figure in the following description.

DETAILED DESCRIPTION

Systems and methods are provided for a multi-scale deep learning-based tomosynthesis image reconstruction, such as a digital breast tomosynthesis (DBT) image reconstruction, that mitigates limited angular artifacts and tissue superposition, and improves in-depth resolution of the resulting images. A multi-scale deep neural network may be used where a first, or low-resolution, network may focus on a first parameter, such as limited angular artifacts reduction, and a second, or high-resolution, network may focus on a second parameter, such as image detail refinement. The output from the first neural network may be used as the input for the second neural network. The systems and methods may reduce the sparse-view artifacts in DBT via deep learning without losing image sharpness and contrast. A multi-scale deep neural network may be trained, such as with two or more unroll-type neural networks, and may be used with a decoupled training for each unroll to reduce training-time computational cost. In some configurations, an ROI loss may be used for further improvement on the resolution and contrast of the images.

In some configurations, a region of interest loss method on microcalcifications may be used to improve the spatial resolution and contrast of the regions of interest, such as on microcalcifications. In a non-limiting example, the network was trained and tested on 176 realistic breast phantoms, and demonstrated improved in-plane contrast (3.17 versus 0.43, p<0.01) and in-depth resolution (1.19 mm versus 4.96 mm, p<0.01) as compared to an iterative reconstruction (IR) method.

Figure 1:
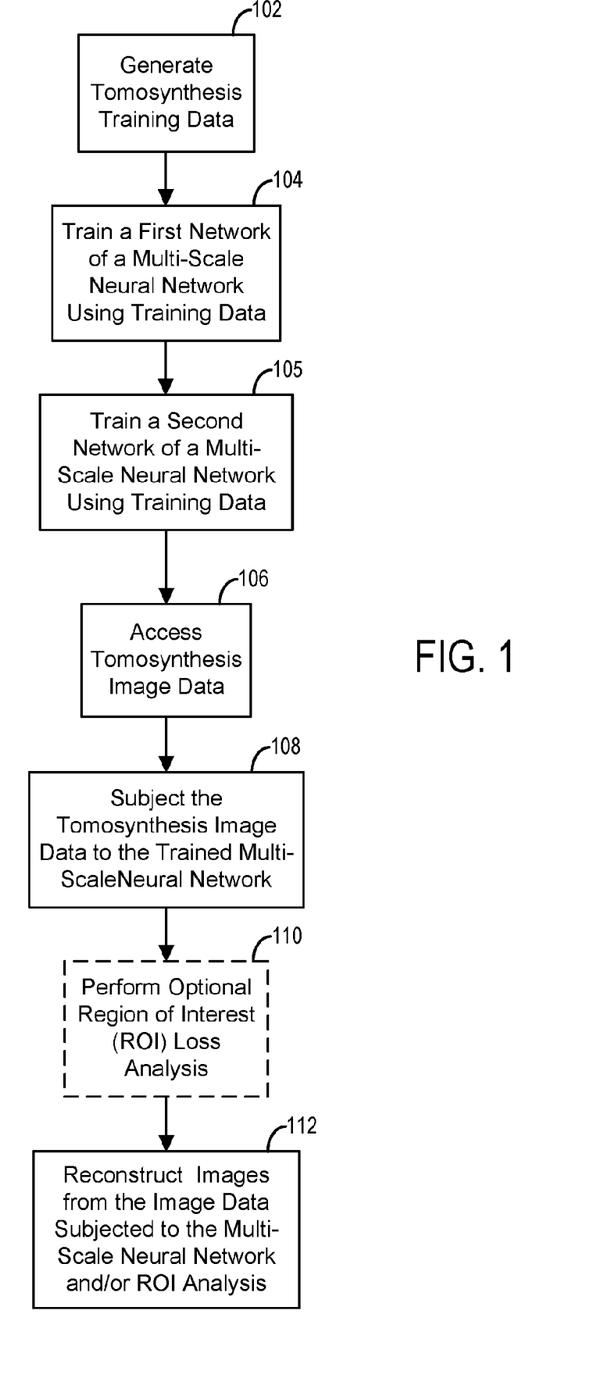
FIG. 1 is a flow chart of non-limiting example steps for a method of tomosynthesis image reconstruction in accordance with the present disclosure.

Referring to FIG. 1, a flow chart of non-limiting example steps for a method of tomosynthesis image reconstruction is shown. Tomosynthesis training data series may be generated at step 102. A first network of a multi-scale neural network may be trained using a first portion of the training data series at step 104. A second network of a multi-scale neural network may be trained using a second portion of the training data series at step 105. The resulting, trained multi-scale neural network may be stored and accessed for later use.

When images of a particular subject are needed, tomosynthesis image data of the subject may be accessed or otherwise acquired at step 106. Tomosynthesis image data may include digital breast tomosynthesis image data. Then, the trained multi-scale neural network can be accessed and the tomosynthesis image data is subjected to the trained multi-scale neural network at step 108. An optional region of interest loss analysis may be performed on the tomosynthesis image data at step 110. Images of the subject may be reconstructed from the image data that was subjected to the neural network and/or the ROI loss analysis to thereby produce, as will be described, images with suppressed artifacts.

Training of a multi-scale neural network may include using realistic breast phantoms or real patients' data. Numerical breast phantoms are a reliable choice for DBT simulation because of the extensive existing studies that have proven the performance of these phantoms. Real patients' data may yet be more precise in some aspects. When training a multi-scale neural network, both dense-view sampling (e.g. 0.5°) and sparse-view sampling may be acquired from the scans. In some configurations, the ROIs may be annotated, such as by a human annotator. These ROIs may contain the sparse-view artifacts in the sparse-view reconstruction results. A deep multi-scale neural network with an ROI loss may be trained to suppress the artifacts while keeping existing structures.

In one configuration, a network of a multi-scale neural network is an unrolled network, which may solve the following optimization problem:

$$x^* = \operatorname*{argmin}_{x} \|Ax - b\|_w^2 + \beta R(x) \quad (1)$$

where x is the image to be reconstructed, A is the system matrix, b is the projection data, w is the noise weighting matrix, R(x) is the prior function, and β is the hyperparameter to balance between data fidelity and the prior knowledge.

Equation (1) can be solved via proximal gradient descent:

$$x^n = \operatorname{prox}_{\gamma \beta R}\{(x^{n-1}) - \gamma A^T w (A x^{n-1} - b)\} \quad (2)$$

where γ is a suitable step size for the gradient descent. The decoupled unrolled network may replace proximal mapping with CNNs and the gradient descent step with separable quadratic surrogate (SQS). The SQS is free of choosing step size γ and has faster convergence. The SQS step may be noted as:

$$g(x) = x - \frac{A^T w(Ax - b)}{A^T A 1} \quad (3)$$

The decoupled unrolled network can be expressed as:

$$x^{(n)} = f(g^M(x^{(n-1)}), x^{(n-1)}; \Theta^{(n)}) \quad (4)$$

where f(y, x; $\Theta^{(n)}$) is a CNN with trainable parameters $\Theta^{(n)}$ and input y and x concatenated along the channel direction. $g^M(x^{(n-1)})$ means Mth iterations of SQS (3) being applied to input image $x^{(n-1)}$. The network was trained sequentially from the first unroll to the last unroll. The training at nth unroll may be expressed as:

$$\Theta^{(n)} = \underset{\Theta}{\mathrm{argmin}} \sum \left\| f\left(g^M\left(x_i^{(n-1)}\right), x_i^{(n-1)}; \Theta\right) - x_i^{ref} \right\| \quad (5)$$

where $x_i^{ref}$ is the label image of the ith training sample, and $x_i^{(n-1)}$ is the output of trained networks for the ith sample. Compared to most unrolled networks which need simultaneously optimization of $\Theta^{(1)}$ to $\Theta^{(N)}$, the decoupled training may only be optimized one $\Theta^{(n)}$ at a time. That is, conventional training techniques suffer from large memory consumption issues when processing 3D volume data, whereas decoupled unrolled network training may train each iteration step separately to reduce memory costs. The feature map size may be significantly reduced, leading to less training memory and time requirement.

Figure 2:
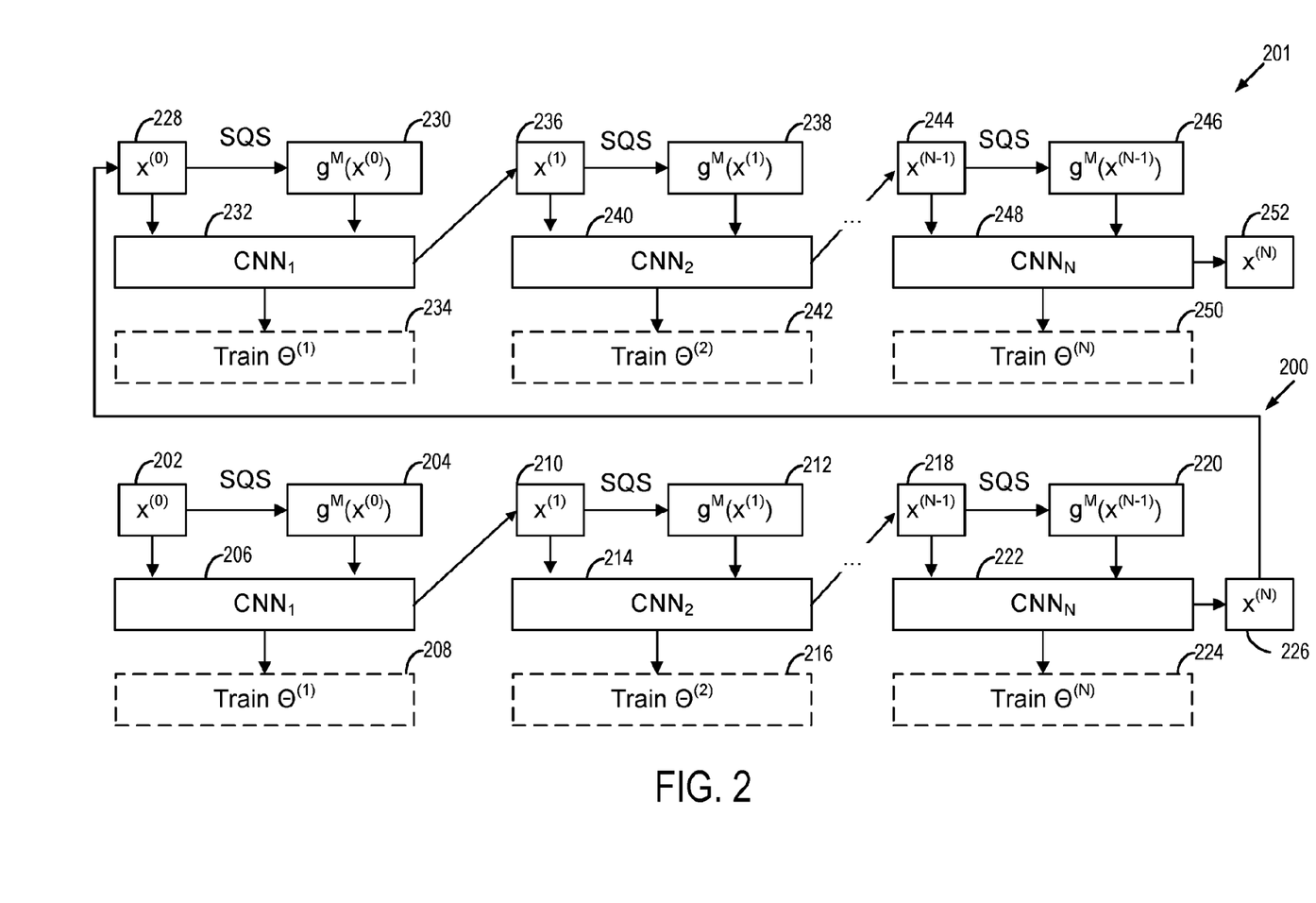
FIG. 2 is a non-limiting example convolutional neural network (CNN) architecture that may be used in accordance with the present disclosure.

Referring to FIG. 2, a non-limiting example multi-scale convolutional neural network architecture in accordance with the present disclosure is shown. The multi-scale convolutional neural network is shown with a first network or low-resolution network 200 and a second network or high-resolution network 201, which may be decoupled unrolled networks. The low-resolution network 200 includes initial input 202, initial separable quadratic surrogate 204, first convolutional neural network level 206, and initial training data 208. The low-resolution network 200 also includes a subsequent input 210, a subsequent separable quadratic surrogate 212, a subsequent convolutional neural network level 214, and subsequent training data 216. This framework extends such that the low-resolution network 200 also includes N-1 input 218, N-1 separable quadratic surrogate 220, N convolutional neural network level 222 and N training data 224. The result from the low-resolution network 200 is delivered via low-resolution network output 226.

The low-resolution network output 226 may be used as an initial input 228 for a high-resolution network 201. The low-resolution network output 226 may be upsampled before being used as the initial input 228. The high-resolution network 201 includes initial input 228, initial separable quadratic surrogate 230, first convolutional neural network level 232, and initial training data 234. The high-resolution network 201 also includes a subsequent input 236, a subsequent separable quadratic surrogate 238, a subsequent convolutional neural network level 240, and subsequent training data 242. This framework extends such that the high-resolution network 201 also includes N-1 input 244, N-1 separable quadratic surrogate 246, N convolutional neural network level 248 and N training data 250. The result from the high-resolution network 201 is delivered via high-resolution network output 252.

Input to the network through initial input 202 and initial input 228 may include reconstructed images or projection data. The use of projection data may provide for further image quality improvement in some configurations.

In some configurations, the multi-scale deep neural network may include where the different low-resolution and high-resolution networks are trained differently, or have different objectives. In a non-limiting example, a low-resolution network may focus on limited angular artifacts reduction and a high-resolution network may focus on image detail refinement. Conventional neural network processing would have no need for different training between different networks in the multi-scale network, as a conventional neural network generates outputs directly based upon the same training across all layers of the conventional network. That is, a conventional network would compile all of the training it receives together in order to generate a single output. A conventional network would not have different networks within it each trained differently.

A low-resolution network or first network of a multi-scale neural network may be first applied to low-resolution data to reduce limited angular artifacts. Low resolution data may include resolutions of 0.5 mm×0.5 mm×1 mm resolution, or below, in non-limiting examples. Upsampling of 0.5 mm×0.5 mm×1 mm resolution data for input to a high-resolution network may include upsampling to 0.075 mm×0.075 mm×0.5 mm, in a non-limiting example.

A high-resolution or second network of a multi-scale neural network may include a high-resolution image reconstruction for image detail refinement. The high-resolution network may be trained to map the input to high-resolution training phantoms. Realistic simulation phantoms, real images, previous subject images, and the like may be used for training the networks. The networks may be trained sequentially, each mapping its input to a training ground truth to mitigate computational costs/burdens.

In some configurations, a reconstruction method may be used, where in the low-resolution step several network steps may be applied gradually to refine the reconstruction results. Between the low- and high-resolution networks iterative reconstruction may be applied. In some configurations, iterative reconstruction methods are used in the low-resolution network and/or the high-resolution network processes.

Referring again to FIG. 2, the non-limiting example multi-scale convolutional neural network architecture shown includes two networks, a first network or low-resolution network 200 and a second network or high-resolution network 201. It is to be appreciated that any number of networks or layers may be used, such as 3, 4, 5, 10, or more networks. Each network may be trained differently, or have different objectives, such as to mitigate angular artifacts, mitigate superposition of tissues, focus on image detail refinement, and the like. In some configurations, two or more network layers of a multi-scale network are trained in the same fashion, or include the same objective.

Non-Limiting Example Region of Interest Loss

Detection of microcalcification is one non-limiting example application of DBT. Microcalcifications could be early signs of breast cancer, and they usually have diameter of several hundred micrometers and significantly higher density compared to breast tissues. Because microcalcifications are extremely small compared to the whole volume, they may provide limited contributions to the training loss and may be ignored by the network during training in some cases. The micorcalcifications may be significantly different from the other breast tissues that a network was trained on, which may led to limited contrast and in-depth resolution improvement of microcalcifications compared to iterative reconstructions. In accordance with the present disclosure, these limitations may be addressed by including the ROI loss in addition to the whole-volume L2 loss. In some configurations, this may be reflected as:

$$\Theta^{(n)} = \underset{\Theta}{\operatorname{argmin}} \sum \frac{1}{J} \| f_i^{(n-1)}(\Theta) - x_i^{ref} \|_2^2 + \lambda \sum_i \sum_{k=1}^{K_i} \frac{1}{J_r K_j} \| E_{ik}(f_i^{(n-1)}(\Theta) - x_i^{ref}) \|_2^2 \quad (6)$$

where J is the total number of voxels of an image; $J_r$ is the total number of voxels of ROIs; $K_i$ is the number of ROIs of sample i; $E_{ik}$ is the masking matrix for ROI k in sample i; λ is a hyperparameter to balance between whole-image loss and ROI loss $f_i^{(n-1)}(\Theta)=f(g^M(x_i^{(n-1)}), x_i^{(n-1)}; \Theta)$ as in equation (5).

Non-Limiting Example Breast Phantom Application

In a non-limiting example, a dataset consisted of 176 realistic breast phantoms derived from breast CT scans of healthy subjects. Each breast CT image was segmented into six classes including skin, adipose, glandular and 3 different mixtures of adipose and glandular. Finite element model was applied to the segmented images to simulate breast compression between 50 to 80 mm. We assigned $\mu=0.456$ cm$^{-1}$ for adipose and $\mu=0.802$ cm$^{-1}$ for glandular and skin. For faster computation, the voxel size was downsampled from 0.25×0.25×0.25 mm³ to 1×1×1 mm³. The downsampling did not interfere with the limited angular artifacts, because the artifacts mostly exists in low frequency.

Calcification points were further inserted into phantoms with μ from 1.011 cm$^{-1}$ to 3.034 cm$^{-1}$, which was corresponding to 10% to 30% of the attenuation coefficient of calcium oxalate at 20 keV. Each calcification point only occupied one single voxel and each patient was randomly assigned 0 to 4 calcification points. The 10% to 30% scale factor was corresponding microcalcifications' diameter of 0.1 mm to 0.3 mm whereas our voxel size was 1 mm.

A detector with pixel size of 0.5×0.5 mm² was used. The projecting geometry was configured where the source to detector distance was 660 mm, source to rotation center distance was 627 mm and the breast was placed 10 mm above the detector surface. The angular sampling was from $-21°$ to $+21°$ with 3° interval, giving 15 views in total. Distance driven projector and backprojector were used for both simulation and reconstruction. Poisson noise was added to the projections assuming $10^5$ initial photons per ray.

In the non-limiting example, 140 patients were randomly selected for training whereas the remaining 36 patients were used for testing. UNet with depth of 4 was used as the CNN in each unroll. An unroll number N=10 and SQS iterations M=10 were used. The initial image $x^{(0)}$ was 10 SQS iterations from zero images. Each unroll was trained by Adam optimizer with learning rate of $10^{-3}$ for 150 epochs. The entire training took approximately 12 hours. For the ROI loss, 9×9×9 ROIs were selected around each inserted calcification point with λ set to 0.1. IR results from 20 iterations of SQS from zero were used for comparison. The number of iterations balanced between noise level and artifacts. The thicknesses of the breast were assumed to be known for both IR and deep learning to further reduce limited angular artifacts. Thickness can be measured by the compressor of DBT scanners.

Deep learning results gave significantly improved contrast for in-plane structures with less superposition. In the non-limiting example, both axial and sagittal views showed a structure where deep learning achieved improved in-plane contrast and better in-depth resolution compared to IR. A calcification point was also zoomed in, and deep learning with ROI loss demonstrated significantly improved contrast compared to IR and L2 loss. In addition, there were obvious wave-like artifacts in the IR result which was caused by the sparse sampling. These artifacts were not present in the deep learning results.

Root mean square errors (RMSE) and structural similarity indices (SSIM) were calculated for each testing images comparing to the ground truth. Both deep learning-based results had significantly improved metrics compared to IR (p<0.01). Furthermore, ROI loss only led to slightly worse overall RMSEs and SSIMs compared to L2 loss. There was no substantial visual difference of the glandular reconstructed using the two losses in FIG. 2.

The contrast and spatial resolution were quantitatively analyzed at the calcification points. For each point, a Gaussian function was used to fit the profile along x, y and z directions in a 21-pixel window. The in-depth resolution was calculated as the full width at half maximum (FWHM) of the Gaussian function along z, and the in-plane resolution was taken as the average of FWHM along x and y direction. The Weber contrast was determined, which may be defined as $$c = \frac{I_{peak} - I_{background}}{I_{background}} \quad (7)$$

where Ipeak is the peak intensity as the peak of the Gaussian function, and Ibackground is the background intensity as the bias of the Gaussian function. ROI loss significantly improved resolution and contrast over L2 loss and IR (p<0.01).

In a non-limiting example, downsampled phantoms were used, but the network may be scaled to larger volumes in applications without additional requirement on computational hardware. The trained networks may also be applied to real DBT data. In a non-limiting example, the trained network was further applied to real DBT data from 15 patients and demonstrated improved in-plane contrast and in-depth resolution. In one of the 15 patients, the upper and lower borders of a concentrated mass can be identified in the network results, which was otherwise indistinguishable in the IR results.

Figure 3:
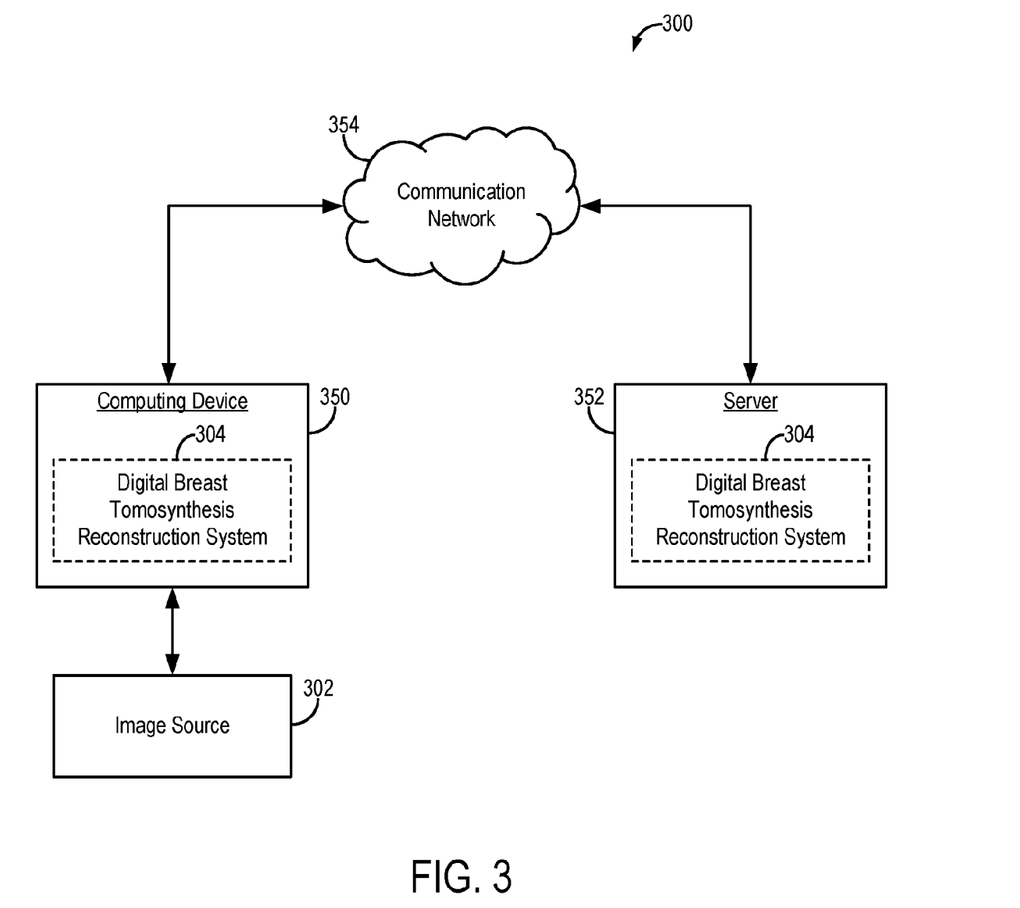
FIG. 3 is a block diagram of an example system that can implement a digital breast tomosynthesis reconstruction system for generating images of a subject using a machine learning or deep learning method.

Referring to FIG. 3, an example of a system 300 for generating and implementing a machine learning or deep learning routine in accordance with some embodiments of the systems and methods described in the present disclosure is shown. As shown in FIG. 3, a computing device 350 can receive one or more types of data (e.g., digital breast tomography, x-ray, computed tomography, ultrasound, multiparametric MRI data, breast image data, and the like) from image source 302. In some embodiments, computing device 350 can execute at least a portion of a digital breast tomosynthesis reconstruction system 304 to generate images of a breast, or otherwise segment a region of interest from data received from the image source 302.

Additionally or alternatively, in some embodiments, the computing device 350 can communicate information about data received from the image source 302 to a server 352 over a communication network 354, which can execute at least a portion of the digital breast tomosynthesis reconstruction system 304 to generate images of a region of interest, or otherwise segment a region of interest from data received from the image source 302. In such embodiments, the server 352 can return information to the computing device 350 (and/or any other suitable computing device) indicative of an output of the digital breast tomosynthesis reconstruction system 304 to generate images of a region of interest, or otherwise segment a region of interest from data received from the image source 302.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, image source 302 can be any suitable source of image data (e.g., measurement data, images reconstructed from measurement data), such as a digital breast tomosynthesis system, another computing device (e.g., a server storing image data), and so on. In some embodiments, image source 302 can be local to computing device 350. For example, image source 302 can be incorporated with computing device 350 (e.g., computing device 350 can be configured as part of a device for capturing, scanning, and/or storing images). As another example, image source 302 can be connected to computing device 350 by a cable, a direct wireless link, and so on. Additionally or alternatively, in some embodiments, image source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
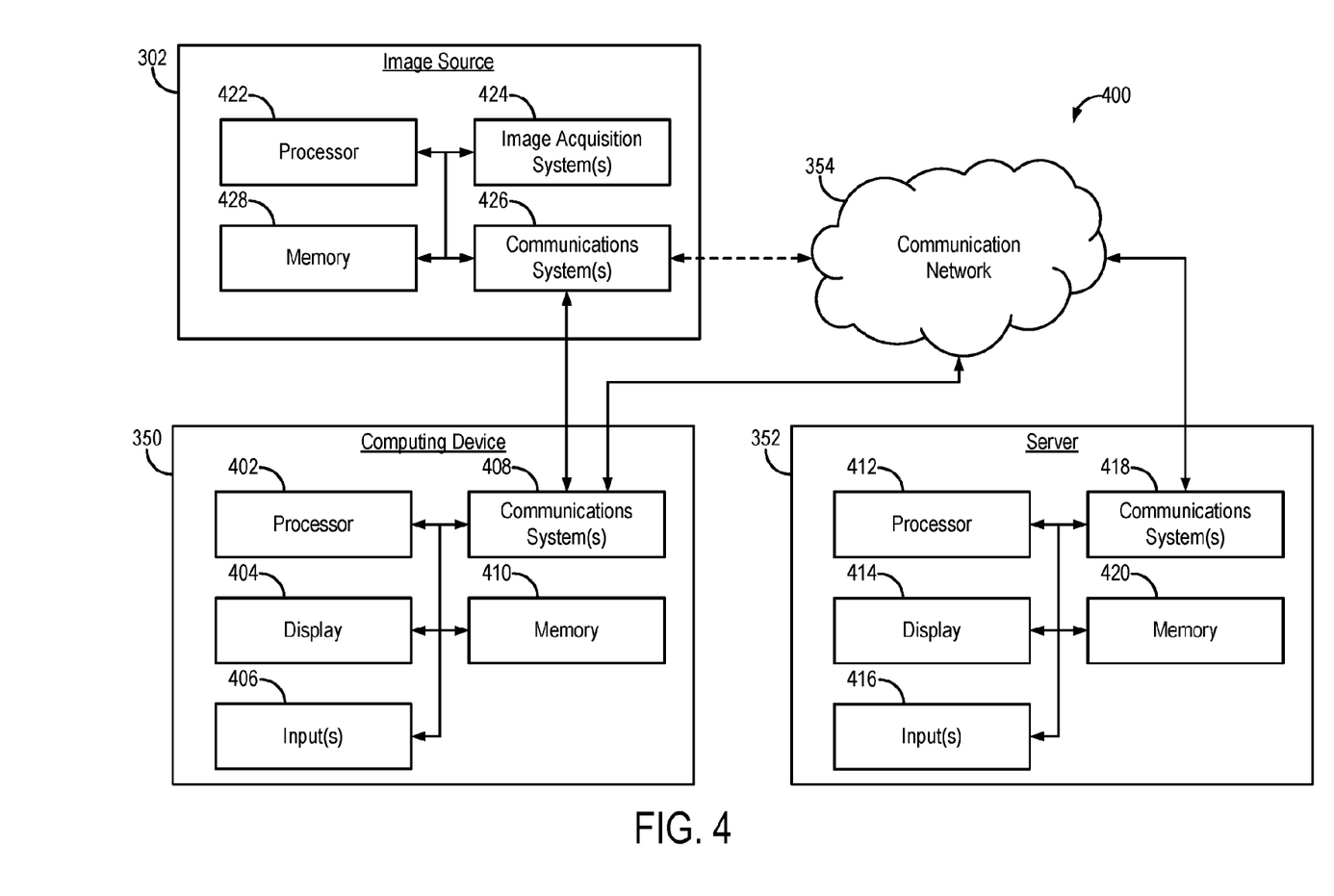
FIG. 4 is a block diagram of example hardware components of the system of FIG. 3.

Referring now to FIG. 4, an example of hardware 400 that can be used to implement image source 302, computing device 350, and server 354 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, image source 302 can include a processor 422, one or more image acquisition systems 424, one or more communications systems 426, and/or memory 428. In some embodiments, processor 422 can be any suitable hardware processor or combination of processors, such as a CPU, a GPU, and so on. In some embodiments, the one or more image acquisition systems 424 are generally configured to acquire data, images, or both, and can include an RF transmission and reception subsystem of a digital breast tomosynthesis system. Additionally or alternatively, in some embodiments, one or more image acquisition systems 424 can include any suitable hardware, firmware, and/or software for coupling to and/or controlling operations of an digital breast tomosynthesis system. In some embodiments, one or more portions of the one or more image acquisition systems 424 can be removable and/or replaceable.

Note that, although not shown, image source 302 can include any suitable inputs and/or outputs. For example, image source 302 can include input devices and/or sensors that can be used to receive user input, such as a keyboard, a mouse, a touchscreen, a microphone, a trackpad, a trackball, and so on. As another example, image source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more image acquisition systems 424, and/or receive data from the one or more image acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of image source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 5:
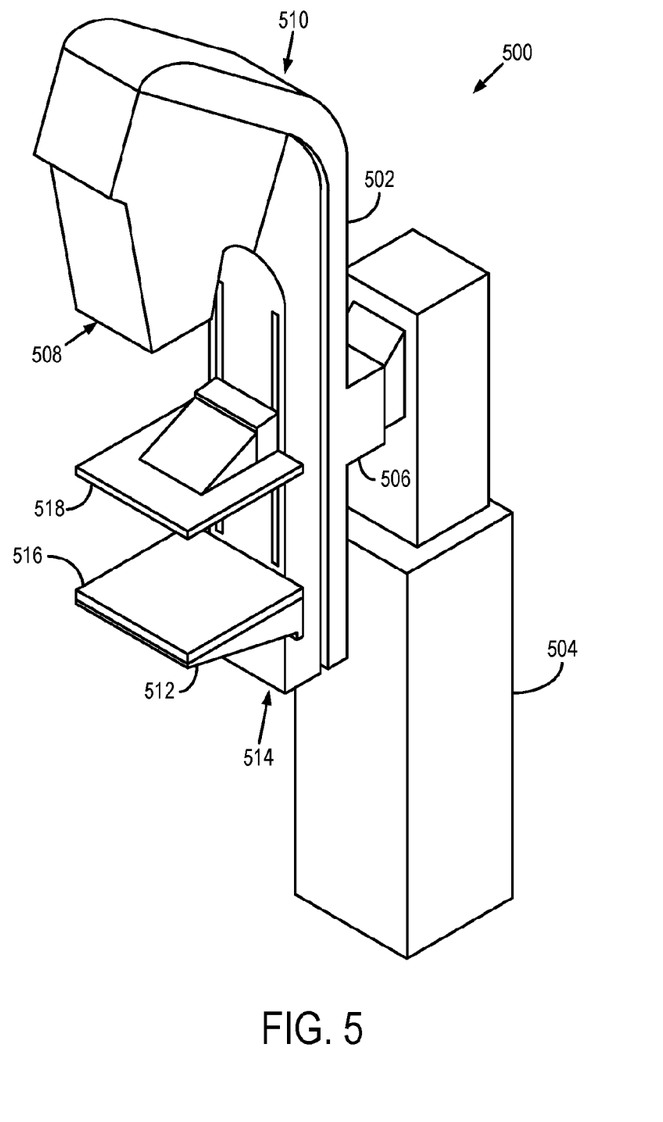
FIG. 5 is a block diagram of a non-limiting example digital breast tomosynthesis (DBT) system.

Referring to FIG. 5, a non-limiting example digital breast tomosynthesis (DBT) system 500 is shown that may be used in accordance with the present disclosure. DBT system 500 may include a drive plate 518 configured to provide compression against a compression plate 516 for an organ disposed between drive plate 518 and compression plate 516. Imaging detectors 512 may be coupled to a mounting system 514. Radiation source 508 may be coupled to support system 502 and coupled to base 504 with rotatable coupler 506.

The present disclosure has described one or more preferred embodiments, and it should be appreciated that many equivalents, alternatives, variations, and modifications, aside from those expressly stated, are possible and within the scope of the invention.

The invention claimed is:

1. A digital breast tomosynthesis system for controlling artifacts in imaging of a subject, the system comprising:
   a base plate, and a compression plate configured to provide compression of an organ disposed between the base plate and the compression plate,
   a rotation support coupled to the base plate and the compression plate to rotate the base plate and the compression plate about the organ to acquire digital breast tomosynthesis image data with a plurality of resolutions;
   a computer system configured to:
   i) access a trained multi-scale neural network including a first resolution network and a second resolution network,
      wherein at least one of the first resolution network or the second resolution network is trained to suppress artifacts using image training data that include at least one artifact, and
      wherein a first resolution of the first resolution network is lower than a second resolution of the second resolution network;
   ii) access the acquired digital breast tomosynthesis image data of the subject that includes a region of interest of the organ;
   iii) subject the acquired digital breast tomosynthesis image data to the trained multi-scale neural network to reconstruct an image of the subject with suppressed artifacts in the region of interest; and
   iv) display the image of the subject with the suppressed artifacts.

2. The digital breast tomosynthesis system of claim 1, wherein the first resolution network is trained to reduce limited angular artifacts and the second resolution network is trained to refine image detail.

3. The digital breast tomosynthesis system of claim 1, wherein the image training data include dense-view sampling data and sparse-view sampling data.

4. The digital breast tomosynthesis system of claim 1, wherein the sparse-view sampling data includes sparse-view artifacts, and wherein the at least one artifact included with the image training data is the sparse-view artifact.

5. A method for artifact reduction in digital breast tomosynthesis imaging of a subject, the method comprising:
   a) accessing a trained multi-scale neural network including a first resolution network and a second resolution network,
      wherein at least one of the first resolution network or the second resolution network is trained to suppress artifacts using image training data that include at least one artifact, and
      wherein a first resolution of the first resolution network is lower than a second resolution of the second resolution network;
   b) accessing digital breast tomosynthesis image data of the subject that includes a region of interest;
   c) subjecting the digital breast tomosynthesis image data to the multi-scale neural network to reconstruct an image of the subject with suppressed artifacts in the region of interest; and
   d) displaying the image of the subject with the suppressed artifacts.

6. The method of claim 5, wherein the first resolution network is trained to reduce limited angular artifacts and the second resolution network is trained to refine image detail.

7. The method of claim 5, wherein the image training data include dense-view sampling data and sparse-view sampling data.

8. The method of claim 5, wherein the sparse-view sampling data include sparse-view artifacts, and wherein the at least one artifact included with the image training data is the sparse-view artifact.

9. The method of claim 5, wherein the multi-scale network is trained using decoupled training that includes optimizing one training parameter at a time.

10. The method of claim 9, wherein at least one of the first or second network is a decoupled trained unroll-type neural network that is a convolutional neural network (CNN) with separable quadratic surrogate.

11. The method of claim 9, wherein the digital breast tomosynthesis image data is subjected to the decoupled trained unroll-type neural network over a plurality of iterations.

12. The method of claim 11, wherein the decoupled trained unroll-type neural network is trained sequentially from a first unroll to a last unroll.

13. The method of claim 5, wherein the digital breast tomosynthesis image data includes microcalcifications.

14. The method of claim 5, further comprising performing a region of interest loss analysis that applies a region-of-interest loss.

15. The method of claim 5, wherein the image training data includes image data of realistic numerical breast phantoms generated from data acquired with at least one of digital breast tomosynthesis, mammography, computed tomography (CT), breast CT, magnetic resonance (MR) or breast MR.

16. A system for artifact reduction in digital breast tomosynthesis imaging of a subject, the system comprising:
   a computer system configured to:
   i) access a trained multi-scale neural network including a first resolution network and a second resolution network,
      wherein at least one of the first resolution network or the second resolution network is trained to suppress artifacts using image training data that include at least one artifact, and
      wherein a first resolution of the first resolution network is lower than a second resolution of the second resolution network;
   ii) access digital breast tomosynthesis image data of the subject that includes a region of interest;
   iii) subject the digital breast tomosynthesis image data to the multi-scale neural network to reconstruct an image of the subject with suppressed artifacts in the region of interest;
   iv) display the image of the subject with the suppressed artifacts.

17. The system of claim 16, wherein the first resolution network is trained to reduce limited angular artifacts and the second resolution network is trained to refine image detail.

18. The system of claim 16, wherein the image training data include dense-view sampling data and sparse-view sampling data.

19. The system of claim 16, wherein the sparse-view sampling data include sparse-view artifacts, and wherein the at least one artifact included with the image training data is the sparse-view artifact.

20. The system of claim 16, wherein the multi-scale network is trained using decoupled training that includes optimizing one training parameter at a time.

21. The system of claim 20, wherein at least one of the first or second network is a decoupled trained unroll-type neural network that is a convolutional neural network (CNN) with separable quadratic surrogate.

22. The system of claim 20, wherein the computer system is further configured to subject the digital breast tomosynthesis image data to the decoupled trained unroll-type neural network over a plurality of iterations.

23. The system of claim 22, wherein the decoupled trained unroll-type neural network is trained sequentially from a first unroll to a last unroll.

24. The system of claim 16, wherein the digital breast tomosynthesis image data includes microcalcifications.

25. The system of claim 16, wherein the computer system is further configured to perform a region of interest loss analysis that applies a region-of-interest loss.

26. The system of claim 25, wherein the region of interest loss analysis applies a region of interest loss that is separate from a whole-volume L2 loss applied by the decoupled trained unroll-type neural network.

27. The method of claim 16, wherein the image training data includes image data of realistic numerical breast phantoms generated from data acquired with at least one of digital breast tomosynthesis, mammography, computed tomography (CT), breast CT, magnetic resonance (MR) or breast MR.

* * * * *